(12) United States Patent
Askill et al.

(10) Patent No.: US 6,521,251 B2
(45) Date of Patent: Feb. 18, 2003

(54) METHODS FOR TREATING BURNS ON MAMMALIAN SKIN TO REDUCE THE RISK OF INFECTION AND TO MINIMIZE FLUID LOSS

(75) Inventors: Ian N. Askill, Colorado Springs, CO (US); Shane Karnik, Colorado Springs, CO (US)

(73) Assignee: Flowers Park Ltd., Cheshire (GB)

( * ) Notice: Subject to any disclaimer, the term of this patent is extended or adjusted under 35 U.S.C. 154(b) by 0 days.

(21) Appl. No.: 09/918,706

(22) Filed: Jul. 27, 2001

(65) Prior Publication Data

US 2002/0037272 A1 Mar. 28, 2002

Related U.S. Application Data

(60) Provisional application No. 60/221,016, filed on Jul. 27, 2000.

(51) Int. Cl.[7] .......................... A61K 9/70; A61K 47/32; A61L 26/00; A61P 17/02
(52) U.S. Cl. ................. 424/443; 514/772.4; 514/772.6; 424/DIG. 13
(58) Field of Search ........................... 514/772.4, 772.6; 424/78.06, DIG. 13, 443

(56) References Cited

U.S. PATENT DOCUMENTS

| 3,654,239 A | 4/1972 | McIntire et al. |
| 5,254,132 A | 10/1993 | Barley et al. |
| 5,306,490 A | 4/1994 | Barley, Jr. |
| 5,403,591 A | 4/1995 | Tighe et al. |
| 5,580,565 A | 12/1996 | Tighe et al. |
| 5,653,789 A | 8/1997 | Henise |
| 5,807,563 A | 9/1998 | Askill et al. |
| 5,902,594 A * | 5/1999 | Greff et al. .................. 424/405 |

FOREIGN PATENT DOCUMENTS

| WO | 93/25196 | 12/1993 |

* cited by examiner

*Primary Examiner*—Edward J. Webman
(74) *Attorney, Agent, or Firm*—Burns, Doane, Swecker & Mathis L.L.P.

(57) ABSTRACT

Disclosed are methods for treating burns on mammalian skin to reduce the risk of infection and to minimize fluid loss. Specifically, the methods of this invention involve the in situ formation of a polymeric cyanoacrylate film at the site of the burn. The cyanoacrylate film acts as a barrier inhibiting the introduction of pathogens (e.g., bacteria) into the burn area and as a barrier for the loss of fluids.

12 Claims, No Drawings

METHODS FOR TREATING BURNS ON MAMMALIAN SKIN TO REDUCE THE RISK OF INFECTION AND TO MINIMIZE FLUID LOSS

CROSS-REFERENCE TO RELATED APPLICATIONS

This application claims the benefit of U.S. Provisional Patent Application Serial No. 60/221,016 filed Jul. 27, 2000 which application is incorporated herein by reference in its entirety.

BACKGROUND OF THE INVENTION

FIELD OF THE INVENTION

This invention is directed to methods for treating burns on mammalian skin to reduce the risk of infection and to minimize fluid loss. Specifically, the methods of this invention involve the in situ formation of a polymeric cyanoacrylate film over the mammalian skin surface at the site of the burn. The cyanoacrylate film acts as a barrier inhibiting the introduction of pathogens (e.g., bacteria) into the burn area and as a barrier for the loss of fluids. Preferably, the cyanoacrylate prepolymer comprises an antimicrobial agent which is incorporated into the polymeric film to further retard the introduction of pathogens into the burn area.

References

The following publications, patent applications and patents are cited in this application as superscript numbers:

1. Barley, "Methods for Retarding Blister Formation by Use of Cyanoacrylate Adhesives", U.S. Pat. No. 5,306,490, issued Apr. 26, 1994.
2. Barley, et al., Methods for Treating Suturable Wounds by Use of Sutures and Cyanoacrylate Adhesives, U.S. Pat. No. 5,254,132, issued Oct. 19, 1993
3. McIntire, et al., Process for the Preparation of Poly(α-Cyanoacrylates), U.S. Pat. No. 3,654,239, issued Apr. 4, 1972
4. Barley, et al., International Patent Application Publication No. WO 93/25196, for Methods for Treating Non-Suturable Wounds by Use of Cyanoacrylate Adhesives, published Dec. 23, 1993
5. Barley, et al., Methods for Reducing Skin Irritation From Artificial Devices by Use of Cyanoacrylate Adhesives, U.S. Pat. No. 5,653,789, issued Aug. 5, 1997
6. Tighe, et al., Methods for Inhibiting Skin Ulceration by Use of Cyanoacrylate Adhesives, U.S. Pat. No. 5,403,591, issued Apr. 4, 1995
7. Tighe, et al., for Use of Cyanoacrylates for Providing a Protective Barrier, U.S. Pat. No. 5,580,565, issued Dec. 6, 1996
8. Askill, et al., for Methods for Draping Surgical Incision Sites, U.S. Pat. No. 5,807,563 issued Sep. 15, 1998

All of the above publications, patent applications and patents are herein incorporated by reference in their entirety to the same extent as if each individual publication, patent application or patent was specifically and individually indicated to be incorporated by reference in its entirety.

State of the Art

Reduced morbidity and/or infection associated with burns on mammalian skin relate directly to the severity of the burn and the level of care provided. Mammalian skin burns are classified into three categories:

first degree burns which are superficial burns characterized by redness and blanching (turns white upon exposure to pressure). First degree burns damage only the top or epidermal layer of the skin and can be associated with low to moderate pain, although severe pain can also arise, and a relatively low risk of infection;

second degree burns which are partial thickness burns. These burns involve the entire epidermis and some portion of the dermis and are associated with moderate to severe pain, a higher risk of infection and loss of body fluid through the exposed dermis; and third degree burns which are full thickness burns involving the entire epidermal and dermal layers. Such burns involve the entire epidermis and the dermis of the burned skin and are associated with severe pain, a very high risk of infection and loss of significant amounts of body fluid.

As is apparent, the risk of infection and morbidity arising from burns increases with the severity of burn and, accordingly, treatment protocols for burns emphasis the need to quickly inhibit the introduction of microbes into the burn site from either endogenous sources or from air borne microbes. In addition, the burn site should be covered with appropriate bandages, etc. to reduce fluid loss and to protect the burn site from further trauma arising from, for example, accidental contact therewith.

However, often bandages and other wound dressings do not inhibit bacterial migration into the burn site because these dressings to not adequately isolate the burn site.

This invention is directed, in part, to the discovery that the in situ formation of a cyanoacrylate polymeric film at the burn site overcomes many of the prior art problems associated with the use of conventional burn dressings. For example, the cyanoacrylate polymer is known in the art to have bacteriostatic properties and the cyanoacrylate monomer permits the inclusion of compatible antimicrobial agents if such is desired. Still another advantage is the formation of an appropriately configured film which completely covers the burn area and forms a water proof film over the skin, thereby inhibiting fluid loss.

The use of cyanoacrylate polymers per this invention is in contrast to their known medical uses as an alternative or adjunct to sutures[2] or as a hemostat[3]. Other described uses of cyanoacrylate prepolymers include their use on mammalian to form polymeric films which are utilized:

to prevent friction blister formation[1], in treating small non-suturable wounds[4], in inhibiting surface skin irritation arising from friction between the skin surface and artificial devices such as tapes, prosthetic devices, casts, etc.[5], as surgical incise drapes[8], in inhibiting skin ulcerations[6], and forming a protective film to inhibit skin degradation due to incontinence.[7]

SUMMARY OF THE INVENTION

This invention is directed to methods for treating the burn site on mammalian skin in order to reduce the risk of infection and to form a waterproof film which inhibits fluid loss from this site.

Such methods involve application of a cyanoacrylate prepolymer composition onto the burn site followed by in situ polymerization of the prepolymer to form a polymeric film. The cyanoacrylate prepolymer composition can be applied as a liquid/gel to the skin surface and can include therapeutic agents such as analgesics, anti-inflammatory agents, antimicrobial agents, etc.

In all but third degree burns, the polymeric film will naturally shed from the skin surface 1–4 days after application and, accordingly, there is no need to effect removal of the film or to cause the skin trauma potentially associated with film removal. This polymeric film forms a bacteriostatic or bactericidal barrier to external sources of burn contamination as well as barrier to fluid loss through the burn site. Moreover, in a preferred embodiment, the cyanoacrylate composition is formulated to contain an antimicrobial agent which, over time, will be released from the resulting film thereby providing for protection against infection at the burn site.

Accordingly, in one of its method aspects, this invention is directed to a method for forming an adherent, surface conforming film at a burn site on the mammalian skin surface of a patient which method comprises:

(a) identifying the extent of the burn site on the mammalian skin surface of the patient;

(b) applying a sufficient amount of a composition comprising a polymerizable cyanoacrylate ester to the burn site defined in (a) above so as to cover this site with the composition; and (c) polymerizing the cyanoacrylate ester so as to form a flexible, waterproof, adhesive polymer layer which adheres to the area(s) where the composition was applied.

Preferably, the polymerizable cyanoacrylate ester comprises an ester which, in monomeric form, is represented by formula I:

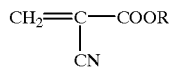

I where
R is selected from the group consisting of:
  alkyl of 1 to 10 carbon atoms,
  alkenyl of 2 to 10 carbon atoms,
  cycloalkyl groups of from 5 to 8 carbon atoms,
  phenyl,
  2-ethoxyethyl,
  3-methoxybutyl,
  and a substituent of the formula:

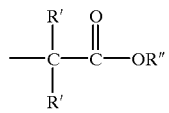

wherein each R' is independently selected from the group consisting of:
    hydrogen and methyl, and
R'' is selected from the group consisting of:
  alkyl of from 1 to 6 carbon atoms,
  alkenyl of from 2 to 6 carbon atoms,
  alkynyl of from 2 to 6 carbon atoms,
  cycloalkyl of from 3 to 8 carbon atoms,
  aralkyl selected from the group consisting of benzyl, methylbenzyl and phenylethyl,
  phenyl, and
  phenyl substituted with 1 to 3 substituents selected from the group consisting of hydroxy, chloro, bromo, nitro, alkyl of 1 to 4 carbon atoms, and alkoxy of from 1 to 4 carbon atoms.

More preferably, in the cyanoacrylate esters of formula I, R is alkyl of from 2 to 10 carbon atoms and more preferably alkyl of from 2 to 8 carbon atoms. Even more preferably, R is butyl, pentyl or octyl and most preferably, R is n-butyl.

In another preferred embodiment, the polymerized cyanoacrylate composition has a thickness of no more than about 1 millimeter and, more preferably, the polymer layer has a thickness of from about 2 to about 500 microns and still more preferably from about 20 to about 100 microns.

DETAILED DESCRIPTION OF THE PREFERRED EMBODIMENTS

This invention is directed to methods for treating burns on mammalian skin to reduce the risk of infection and to minimize fluid loss.. However, prior to discussing this invention in further detail, the following terms will first be defined.

Definitions

As used herein, the following terms have the following meanings:

The term "burn site" refers to the mammalian skin surface which has suffered first, second and/or third degree burns as well as the immediate area adjacent to the burn. This immediate area typically extends at least 0.1 to 2 inches (0.254 to 5.08 cm) in all directions beyond the burn. The mammalian skin burn can be caused by any number of sources including, by way of example, heat burns, chemical burns, sun burns, etc.

The term "polymerizable cyanoacrylate esters" refers to polymerizable formulations comprising cyanoacrylate monomers or polymerizable oligomers which, in their monomeric form, are preferably compounds represented by formula I as described above.

More preferably, in formula I, R is an alkyl group of from 2 to 10 carbon atoms including ethyl, n-propyl, iso-propyl, n-butyl, iso-butyl, sec-butyl, n-pentyl, iso-pentyl, n-hexyl, iso-hexyl, 2-ethylhexyl, n-heptyl, octyl, nonyl, and decyl. More preferably, R is butyl, pentyl or octyl and most preferably, R is n-butyl. Mixtures of such compounds can also be employed as disclosed by Berger, et al., U.S. Pat. No. 5,998,472 which is incorporated herein by reference in its entirety.

A preferred cyanoacrylate ester for use in the invention is n-butyl-2-cyanoacrylate.

The polymerizable cyanoacrylate esters described herein rapidly polymerize in the presence of water vapor or tissue protein, and the n-butyl-cyanoacrylate bonds to mammalian skin tissue without causing histotoxicity or cytotoxicity.

Such polymerizable cyanoacrylate esters are sometimes referred to herein as prepolymers and compositions comprising such esters are sometimes referred to herein as prepolymer compositions.

Polymerizable cyanoacrylate esters are known in the art and are described in, for example, U.S. Pat. Nos. 3,527,224; 3,591,676; 3,667,472; 3,995,641; 4,035,334; and 4,650,826 the disclosures of each are incorporated herein by reference in their entirety.

The term "biocompatible plasticizer" refers to any material which is soluble or dispersible in the cyanoacrylate composition, which increases the flexibility of the resulting polymeric film coating on the skin surface, and which, in the amounts employed, is compatible with the skin as measured by the lack of moderate to severe skin irritation. Suitable plasticizers are well known in the art and include those disclosed in U.S. Pat. Nos. 2,784,127 and 4,444,933 the disclosures of both of which are incorporated herein by reference in their entirety. Specific plasticizers include, by way of example only, acetyl tri-n-butyl citrate (preferably ~20 weight percent or less), acetyl trihexyl citrate (preferably ~20 weight percent or less) butyl benzyl phthalate, dibutyl phthalate, dioctylphthalate, n-butyryl tri-n-hexyl citrate, diethylene glycol dibenzoate (preferably ~20 weight percent or less) and the like. The particular biocompatible plasticizer employed is not critical and preferred plasticizers include dioctylphthalate and $C_2$–$C_4$-acyl tri-n-hexyl citrates.

The term "antimicrobial agent" refers to agents which destroy microbes (i.e., bacteria, fungi, yeasts and viruses) thereby preventing their development and their pathogenic action.

Methods

The methods of this invention comprise the in situ formation of a cyanoacrylate polymer film on the skin surface at the burn site of a patient which polymeric film acts as a barrier film in inhibiting the introduction of pathogens into the burn and the removal of fluids from the burn.

The treatment protocol preferably involves skin preparation prior to in situ formation of the cyanoacrylate polymer film at the burn site. Specifically, the burn site is conventionally treated by the attending health care professional by cleaning with an appropriate antimicrobial composition. The burn site is preferably dried, e.g., blotted dry, and then an adherent polymeric film is formed over this site by applying a cyanoacrylate composition to the burn site. As noted above, this composition comprises polymerizable cyanoacrylate monomers and/or reactive oligomers which, upon contact with the burn site polymerizes in situ to form a polymeric film.

Polymerization occurs at ambient conditions for a sufficient period of time to allow polymerization to proceed. In general, the particular length of time required for polymerization will vary depending on factors such as the amount of adhesive composition applied, the temperature of the burn site, the moisture content of the burn site, the surface area of burn site, and the like. However, in a preferred embodiment, polymerization is generally complete within about 10 to about 60 seconds while the burn site is maintained at ambient conditions; however, in some cases, polymerization can occur up to about 5 minutes. During this period, the patient is maintained in a position which permits the cyanoacrylate to polymerize and form a polymeric film while minimizing any patient movement which might dislodge the cyanoacrylate from that burn site or create undesirable bonding.

Sufficient amounts of the composition are employed to cover (i.e., coat) the entire burn site with a layer of the cyanoacrylate polymer. If necessary, excess cyanoacrylate monomer and/or oligomer can be removed with a wipe or tissue paper before polymerization or, after polymerization, any polymer formed at unintended sites can be removed with materials such as acetone.

After polymerization, the resulting polymeric film forms a barrier film which strongly adheres to the skin, is flexible and waterproof. Such strong adherence effectively eliminates the possibility that the film will separate from the patient. However, notwithstanding such strong adherence, the polymeric film will only adhere to the burn site for first and second degree burns for a period of about 1–4 days after which time it sloughs off. This occurs because the cyanoacrylate polymer is adhering only to the epidermal layer which is continuously in the process of being sloughed off and replaced by the underlying cells. Accordingly, the cyanoacrylate film need not be removed from such burn sites.

For third degree burns, it may be necessary to remove the polymeric film because such burns typically extend beyond the epidermal layer of the patient. In such cases, the film can be removed by conventional means described above. In any event, the application of a polymeric film to third degree burns beneficially reduces the rate of infection and fluid loss.

The polymeric film should be maintained in an unbroken manner over the entire burn site. This can be assured by careful application of the cyanoacrylate adhesive onto the burn site. Additionally, the use of a plasticizer will facilitate the maintenance of the polymeric film in an unbroken manner and will inhibit cracking of the film.

In one embodiment, after application of the initial polymeric layer, a second, preferably thinner, layer is applied thereto. Additional amounts of cyanoacrylate adhesive composition can be applied as needed to maintain an unbroken coating covering over the burn site.

Application is conducted under conditions wherein the polymeric film preferably has a thickness of no more than about 1 millimeter and, more preferably, the polymer layer has a thickness of from about 2 to about 500 microns and still more preferably from about 20 to about 100 microns. If thinner polymeric films are desired, then the polymeric film should have a thickness of from about 2 to about 50 microns and preferably from 10 to 40 microns. The amount of cyanoacrylate composition applied to a unit area to obtain such thicknesses is well within the skill of the art.

The size and thickness of the polymeric film formed onto the burn area can be readily controlled by the amount and viscosity of cyanoacrylate adhesive composition packaged in a single dose product or by use of a multiple use dispenser which governs the amount of material applied onto a unit area of surface skin. In this regard, the dispenser described by Otake, U.S. Pat. No. 4,958,748, which is incorporated by reference in its entirety, is one example of a dispenser which dispenses the cyanoacrylate adhesive composition in a controlled dropwise manner. Other methods for the controlled dispersement of the cyanoacrylate adhesive include, by way of example, a spray applicator, brush, wipe, swab or solid paddle applicator, applicators for repeated and intermittent use of the cyanoacrylate composition and the like.

In applicators, the cyanoacrylate composition is stored at ambient conditions and can be provided in sterile form.

Compositions

The cyanoacrylate compositions comprising the polymerizable cyanoacrylate esters are prepared by conventional methods of mixing the appropriate components until homogenous.

The specific viscosity of these compositions depends, in part, on the intended application of the composition. For example, relatively low viscosities are often preferred where application is to be made to a large surface area (e.g., abdominal surfaces). This preference results from the fact that those forms are less viscous and, accordingly, will permit more facile large surface area application of a thin application. Contrarily, where application is to be made to a specific position on the skin (e.g., elbow surfaces, knee surfaces and the like), higher viscosity compositions, including those containing thixotropic materials, are preferred to prevent "running" of the compositions to unintended locations.

Accordingly, these compositions have a viscosity of from about 2 to 50,000 centipoise at 20° C. Preferably the less viscous compositions have a viscosity of from about 2 to 1,500 centipoise at 20° C. More preferably, the cyanoacrylate ester employed in these compositions is almost entirely in monomeric form and the composition has a viscosity of from about 5 to about 500 centipoise at 20° C.

A thickening agent is optionally employed to increase the viscosity of the composition, which thickening agent is any biocompatible material which increases the viscosity of the composition. Suitable thickening agents include, by way of example, polymethyl methacrylate (PMMA) or other preformed polymers soluble or dispersible in the composition, a suspending agent such as fumed silica and the like with PMMA being preferred. Fumed silica is particularly useful in producing a gel for topical application having a viscosity of from about 1500 to 50,000 centipoise at 20° C. Suitable thickening agents for the compositions described herein also include a partial polymer of the alkyl cyanoacrylate as disclosed in U.S. Pat. Nos. 3,654,239 and 4,038,345 both of which are incorporated herein by reference in their entirety.

Thickening agents are deemed to be biocompatible if they are soluble or dispersible in the composition and are compatible with the skin as measured by the lack of moderate to severe skin irritation.

The cyanoacrylate adhesive compositions preferably include a biocompatible plasticizer and such plasticizers are preferably included in the composition from about 10 to 30 weight percent and more preferably from about 18 to 25 weight percent based on the total weight of the composition absent any antimicrobial agent.

Additionally, the cyanoacrylate compositions described herein preferably include a polymerization inhibitor in an effective amount to inhibit premature polymerization of the composition during storage. In a particularly preferred embodiment, this inhibitor is sulfur dioxide which is employed at from about 50 to 500 ppm, preferably 200 to 500 ppm, based on the total weight of the composition absent any antimicrobial agent. Other preferred polymerization inhibitors include glacial acetic acid, free radical inhibitors (e.g., hydroquinones) and the like which can be used alone or in combination with $SO_2$.

The polymerizable cyanoacrylate ester compositions may additionally contain one or more optional additives such as medicaments, colorants, perfumes, anti-diffusion agents, rubber modifiers, modifying agents, etc. In practice, each of these optional additives should be both miscible and compatible with the cyano-acrylate composition and the resulting polymer. Compatible additives are those that do not prevent the use of the cyanoacrylates in the manner described herein.

In general, colorants are added so that the polymer layer formed on the skin will contain a discrete and discernable color. Perfumes are added to provide a pleasant smell to the formulation. Rubber modifiers are added to further enhance the flexibility of the resulting polymer layer. Medicaments are added as necessary to achieve a desired prophylactic or therapeutic effect. The amount of each of these optional additives employed in the composition is an amount necessary to achieve the desired effect.

Preferred cyanoacrylate compositions useful in the practice of this invention are also disclosed by Greff, et al., U.S. Pat. No. 5,480,935, which application is incorporated herein by reference in its entirety. In a particularly preferred embodiment, the cyanoacrylate adhesive composition further comprises an antimicrobially effective amount of a compatible antimicrobial agent. Such compositions preferably comprise from about 1 to about 40 and preferably 5 to 30 weight percent of the compatible antimicrobial agent either as a solution or as a suspension based on the total weight of the composition. Compatible antimicrobial agents are those which are either soluble or suspendable in the cyanoacrylate composition, which do not cause premature polymerization of the cyanoacrylate composition, which do not prevent polymerization of the cyanoacrylate composition when applied to mammalian skin, and which are compatible with the intended use including biocompatibility with the patient's skin. Suitable such compositions are disclosed in U.S. patent application Ser. Nos. 08/913,681 which discloses compositions of cyanoacrylate/povidone-iodine complexes and 09/215,078 which discloses compositions of cyanoacrylate esters/iodine complexes of polyoxyalkylene polymers. Both applications are incorporated herein by reference in their entirety.

In a particularly preferred embodiment, the compatible antimicrobial agent comprises a complex of iodine molecules with a biocompatible polymer. Such complexes are well known in the art and the resulting complex typically comprises both available iodine and iodide anions. These complexes, on contact with mammalian skin, provide for a source of antimicrobial iodine. In any event, such complexes are employed only as starting materials herein and, by themselves, do not form a part of this invention. Suitable biocompatible polymers include, by way of example only, polyvinylpyrrolidone polymer which, when complexed with iodine, is also referred to under the common name of povidone-iodine available from BASF, Mt. Olive, N.J., USA. When povidone-iodine is employed in the cyanoacrylate composition, it is preferably from about 5 to about 40 weight percent and more preferably from about 10 to 25 weight percent is added to the cyanoacrylate composition based on the total weight of the composition.

Other suitable antimicrobial agents include complexes of iodine molecules with copolymers of vinylpyrrolidone and vinyl acetate, copolymers of vinylpyrrolidone and vinyl acetate cross-linked with polyisocyanates, copolymers of vinylpyrrolidone and vinyl functionalities, polymers of pyrrolidone and the like. Preferably, however, the iodine containing polymer is Povidone Iodine which is commercially available from a number of sources.

The use of a compatible antimicrobial agent in the composition permits the agent to be released from the polymeric film thereby reducing microbial growth under the film.

Other medicaments suitable for use in conjunction with the cyanoacrylate composition include corticoid steroids such as described by Greff, et al. in U.S. Pat. No. 5,962,010 which is incorporated herein by reference in its entirety and analgesic compounds such as lidocaine. The former reduces inflammation at the site of the burn whereas the latter reduces pain. Combinations of a steroid with an analgesic are also covered.

Utility

The methods described herein are useful in forming a polymeric film over the burn site of a mammalian patient. The polymeric film finds particular utility in inhibiting microbial contamination at the burn site while also retarding loss of fluids from this site. Such mammalian patients preferably include humans as well as domestic animals such as horses, cows, dogs, sheep, cats, etc. The maintenance of the polymeric film over the burn site is expected to reduce the incidence of infection by inhibiting microbial contamination at this site.

The following examples illustrate certain embodiments of the invention but is not meant to limit the scope of the claims in any way.

Examples 1–4 below illustrate how methods for treating burns could be practiced.

EXAMPLE 1

A 35 year old female with a simple third degree burn on her upper right thigh resulting from a cooking oil scald is essentially free of damaged tissue following removal of clothing welded to the damaged skin. The wound is highly exudative and is treated by blotting the exposed tissue with a gauze pad and then immediately spraying with a formulation containing 80% n-butyl cyanoacrylate and 20% tri-n-butyl acetyl citrate. The coating rapidly sets to form a milky, semi-transparent protective film over the wound and fluid loss ceases immediately. After 5 days, fresh red tissue is seen growing under the film and the film begins to flake off. The exposed new tissue is covered with silver sulfadiazine cream and gauze for the following 10 days, when an autograft is used to cover the wound. The autograft is sealed at the edges and protected by a further spray of the same barrier formulation. Incorporation of the autograft is rapid and complete.

EXAMPLE 2

A 65 year old male has a 30% BSA burn including significant areas of third degree. The buttocks area has some $3^{rd}$ degree burns and is therefore both highly exudative and very prone to infection. This area is treated by painting with a formulation containing 78% n-butyl cyanoacrylate, 20% tri-n-butyl acetyl citrate, and 2% poloxamer iodine composition sufficient to give an available iodine concentration of 0.2% $I_2$. The artificial barrier film is formed within 30 seconds and exudate stops immediately. Fresh formulation is applied whenever flaking or leakage is noticed. The would progresses by healing under the barrier film. After 4 weeks, the barrier film, is removed with an adhesive remover solution containing 80% m-pyrol, 10% IPA and 10% water. Autograft placement and healing occur uneventfully.

EXAMPLE 3

A 16 year old female with painful superficial $2^{nd}$ degree burns of the lower abdomen is treated with a formulation containing 70% n-butyl cyanoacrylate, 28% tri-n-butyl acetyl citrate and 2% miconized PVP-$I_2$. The formulation is applied after shaking to suspend the PVP-$I_2$, by spraying with a commercially available "mister" for moistening the leaves of houseplants. Pain reduction is almost immediate after curing of the film. The subject is provided with a small bottle of the formulation and several application sponges to reinforce and replace the barrier film over the subsequent 10 days. Pain and exudate have ceased after 12 days. After 30 days, the burn area is fully re-epithelialized and scarring is slight.

EXAMPLE 4

A 45 year old male with extensive first and second degree burns of his left arm is treated over the damaged area with a spray of 80% n-butyl cyanoacrylate, 20% di-ethylhexyl phthalate (DOP) containing 0.1% lidocaine. The formulation forms a milky transparent film within 30 seconds and pain is immediately reduced. This initial film is over-coated every 3 days as necessary to maintain the barrier, with 80% n-butyl cyanoacrylate, 20% DOP formulation. After 12 days the film is allowed to shed naturally. Healing occurs uneventfully.

From the foregoing description, various modifications and changes in the composition and method will occur to those skilled in the art. All such modifications coming within the scope of the appended claims are intended to be included therein.

What is claimed is:

1. A method for forming an adherent, surface conforming film at a burn site on the mammalian skin surface of a patient which method comprises:
    (a) identifying the extent of the burn site on the mammalian skin surface of the patient;
    (b) applying a sufficient amount of a composition comprising a polymerizable cyanoacrylate ester to the burn site defined in (a) above so as to cover this site with the composition; and
    (c) polymerizing the cyanoacrylate ester so as to form a flexible, waterproof, adhesive polymer layer which adheres to the area(s) where the composition was applied.

2. The method according to claim 1 wherein said polymerizable cyanoacrylate ester composition comprises a cyanoacrylate ester, which in monomeric form, is represented by formula I:

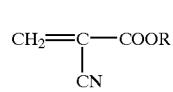

where
    R is selected from the group consisting of:
        alkyl of 1 to 10 carbon atoms,
        alkenyl of 2 to 10 carbon atoms,
        cycloalkyl groups of from 5 to 8 carbon atoms,
        phenyl,
        2-ethoxyethyl,
        3-methoxybutyl,
        and a substituent of the formula:

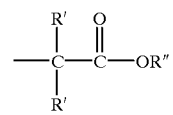

wherein each R' is independently selected from the group consisting of:
            hydrogen and methyl, and
    R" is selected from the group consisting of:
        alkyl of from 1 to 6 carbon atoms,
        alkenyl of from 2 to 6 carbon atoms,
        alkynyl of from 2 to 6 carbon atoms,
        cycloalkyl of from 3 to 8 carbon atoms,
        aralkyl selected from the group consisting of benzyl, methylbenzyl and phenylethyl,
        phenyl, and
        phenyl substituted with 1 to 3 substituents selected from the group consisting of hydroxy, chloro, bromo, nitro, alkyl of 1 to 4 carbon atoms, and alkoxy of from 1 to 4 carbon atoms.

3. The method according to claim 2 wherein R is alkyl of from 2 to 10 carbon atoms.

4. The method according to claim 3 wherein R is alkyl of from 2 to 8 carbon atoms.

5. The method according to claim 4 wherein R is selected from the group consisting of butyl, pentyl or octyl.

6. The method according to claim 5 wherein R is n-butyl.

7. The method according to claim 1 wherein said cyanoacrylate adhesive composition further comprises an antimicrobially effective amount of a compatible antimicrobial agent.

8. The method according to claim 7 wherein the compatible antimicrobial agent is polyvinylpyrrolidone iodine.

9. The method according to claim 1 wherein said cyanoacrylate adhesive composition further comprises a biocompatible plasticizer.

10. The method according to claim 9 wherein said biocompatible plasticizer is dioctyl phthalate.

11. The method according to claim 1 wherein said cyanoacrylate adhesive composition further comprises a polymerization inhibitor.

12. The method according to claim 11 wherein said polymerization inhibitor is $SO_2$.

* * * * *